United States Patent
Lamoise et al.

(10) Patent No.: US 10,828,103 B2
(45) Date of Patent: Nov. 10, 2020

(54) DERMATOLOGICAL TREATMENT DEVICE

(71) Applicant: URGO RECHERCHE INNOVATION ET DEVELOPPEMENT, Chenôve (FR)

(72) Inventors: Michel Lamoise, Bessey les Citeaux (FR); Guirec Le Lous, Paris (FR)

(73) Assignee: URGO RECHERCHE INNOVATION ET DEVELOPPEMENT, Chenôve (FR)

( * ) Notice: Subject to any disclaimer, the term of this patent is extended or adjusted under 35 U.S.C. 154(b) by 97 days.

(21) Appl. No.: 16/068,246

(22) PCT Filed: Jan. 6, 2017

(86) PCT No.: PCT/EP2017/000014
§ 371 (c)(1),
(2) Date: Jul. 5, 2018

(87) PCT Pub. No.: WO2017/118607
PCT Pub. Date: Jul. 13, 2017

(65) Prior Publication Data
US 2019/0021794 A1    Jan. 24, 2019

(30) Foreign Application Priority Data
Jan. 7, 2016    (FR) ..................... 16 00037

(51) Int. Cl.
*A61B 18/20*    (2006.01)
*A61N 5/06*    (2006.01)
(Continued)

(52) U.S. Cl.
CPC ............ *A61B 18/203* (2013.01); *A61B 50/00* (2016.02); *A61N 5/0616* (2013.01);
(Continued)

(58) Field of Classification Search
CPC .... A61B 18/20–18/28; A61N 5/06–2005/073; A61F 7/00–2007/126; A61H 2201/02–2201/107
See application file for complete search history.

(56) References Cited

U.S. PATENT DOCUMENTS 5,354,323 A * 10/1994 Whitebook ............ A61B 18/20 606/11
5,409,481 A *  4/1995 Poppas .................. A61B 18/22 606/12
(Continued)

FOREIGN PATENT DOCUMENTS

| DE | 102013017912 A1 | 4/2015 |
| FR | 2938179 A1 | 5/2010 |
| WO | 2011080574 A1 | 7/2011 |

OTHER PUBLICATIONS

Wikipedia "Nominal"; https://en.wikipedia.org/wiki/Nominal (Year: 2020).*

(Continued)

*Primary Examiner* — Jonathan T Kuo
(74) *Attorney, Agent, or Firm* — Leason Ellis LLP

(57) ABSTRACT

The invention relates to a dermatological treatment device (1) including a laser head (2) capable of shooting a laser beam (3) towards a target region (4) of the skin (5) of a patient, a pyrometer (6) capable of measuring the temperature (T) of the skin (5) in said target region (4), a timer (7) capable of measuring the duration (D) of the laser shot, and a control means (8) capable of selectively activating or deactivating a laser shot, the control means (8) being configured to deactivate the laser shot when the duration (D) of the shot reaches a duration threshold in seconds (Sd) as determined by a linear function in the form $Sd=(To-T)/C$, (Continued)

where T is the measured temperature (T) of the skin, To is a target temperature, and C is an average heating coefficient of the skin.

11 Claims, 1 Drawing Sheet

(51) Int. Cl.
    *A61B 50/00*     (2016.01)
    *A61B 18/00*     (2006.01)
    *A61N 5/067*     (2006.01)

(52) U.S. Cl.
    CPC ............... *A61B 2018/00005* (2013.01); *A61B 2018/0047* (2013.01); *A61B 2018/00452* (2013.01); *A61B 2018/00636* (2013.01); *A61B 2018/00642* (2013.01); *A61B 2018/00666* (2013.01); *A61B 2018/00708* (2013.01); *A61B 2018/00791* (2013.01); *A61B 2018/00809* (2013.01); *A61N 2005/067* (2013.01)

(56) References Cited

U.S. PATENT DOCUMENTS

| | | | | |
|---|---|---|---|---|
| 2006/0041289 A1* | 2/2006 | Cense | ................ | A61B 18/203 607/88 |
| 2013/0066403 A1* | 3/2013 | Giraud | ................ | A61B 18/203 607/89 |
| 2015/0224332 A1* | 8/2015 | Hewitson | ................ | A61N 5/06 607/89 |

OTHER PUBLICATIONS

FR2938179 Espacenet English Translation (Year: 2010).*
International Search Report in corresponding International Patent Application No. PCT/EP2017/000014, dated Mar. 20, 2017. 6 pages.
International Preliminary Report on Patentability in corresponding International Patent Application No. PCT/EP2017/000014, dated Jul. 10, 2018. 6 pages.

* cited by examiner

DERMATOLOGICAL TREATMENT DEVICE

CROSS-REFERENCE TO RELATED PATENT APPLICATIONS

The present patent application is a U.S. National Stage Application under 35 U.S.C. § 371 of International Patent Application No. PCT/EP2017/000014, filed Jan. 6, 2017, which claims the priority of French patent application FR 16/00037 filed on Jan. 7, 2016, both of which are incorporated into the present patent application by reference in their entireties. The International Application was published on Jul. 13, 2017, as International Publication No. WO 2017/118607 A1.

FIELD OF THE INVENTION

The present invention relates to a dermatological treatment device comprising a laser head able to fire a laser beam.

PRIOR ART

Dermatological treatment devices are known, which are typically used to create determined and localized heating of a target zone corresponding to a wound of a patient, which comprises dermal tissues, in order to accelerate healing. Such a dermatological treatment device is for example illustrated by the device described in international application PCT WO 2009/071592 by the Applicant.

In order for such a healing effect to occur optimally, the laser shot should heat the dermal tissues illuminated by the latter until they approach an optimal temperature (comprised between 45 and 55° C.), but without exceeding a maximal temperature (of about 60° C.) that may cause burns or irreversible damage of the dermal tissue.

In order to determine the temperature of the dermal tissues during firing, it is possible to attach a pyrometer to the dermatological treatment device. Such a device is for example described in international application PCT WO 2011/080574 by the Applicant.

Now, and in order to monitor the temperature of the skin at the target zone of the laser firing, a control means of the laser firing should be used capable of selectively activating or deactivating a laser firing.

It is known in the field of dermatological treatment devices to monitor the quantity of heat transmitted to the tissues by the laser shot by limiting the duration of a shot to a constant value. Thus, a previous model by the applicant applies shots with a constant power, for example of 6 W, according to a duration configurable from among two values: 10 or 13 s. Now, such an approach neglects too many parameters, such as the variability of the behaviors of the skin from one patient to another, and leads to excessive variability of the temperature reached. Two risks then exist: an excessive temperature of the skin is reached, causing burns, or conversely, too low a temperature makes the treatment ineffective. Means should therefore be proposed to control laser firing more precisely.

SUMMARY OF THE INVENTION

The present invention resolves these various drawbacks and proposes control means able to monitor the laser firing based on the temperature of the skin and a variable firing duration.

The invention relates to a dermatological treatment device comprising a laser head capable of shooting a laser beam towards a target region of the skin of a patient, a pyrometer capable of measuring the temperature (T) of the skin in said target region, a timer capable of measuring the duration (D) of the laser shot, and a control means capable of selectively activating or deactivating a laser shot, the control means being configured to deactivate the laser shot when the duration (D) of the shot reaches a duration threshold in seconds (Sd) as determined by a linear function in the form Sd=(To−T−b)/C, where T is the measured temperature (T) of the skin, To is a target temperature, and C is an average heating coefficient of the skin.

The objective temperature To corresponds to the temperature objective or targeted temperature.

The temperature offset corresponds to a corrective value, said value having been determined by the inventors so as to account for the sensitivity/precision of the materials in particular. It may involve a constant or a value varying based on the temperature; preferably this temperature offset is a constant.

The average heating coefficient of the skin is a value taking account of the variation of the measured temperature T of the skin as a function of the time (in ° C. per s$^{-1}$), this value being able to be determined for a given patient population.

In the device according to the invention, the variation of the temperature of the skin is monitored with time and dynamically by the pyrometer. Advantageously, the duration threshold Sd is determined immediately before or immediately after the beginning of the laser shot, preferably immediately after the beginning of the laser shot, i.e., preferably in the second following the beginning of the laser shot. Also advantageously, the duration threshold can be reevaluated during the laser shot once, twice or several times.

Advantageously, the control means is also configured to deactivate the laser shot when the temperature (T) reaches a temperature threshold (St).

The control means is then configured to deactivate the laser once one of the two thresholds is reached, either the temperature (T) of the skin has reached the temperature threshold (St) or the duration of the shot has reached the maximum duration Sd as determined by the previously defined affine function.

The invention also relates to a dermatological treatment system, said system comprising a device as described above and interaction means between said laser head and the skin zone to be treated, said interaction means being arranged to cooperate with said slaving means.

The invention lastly relates to a dermatological treatment method implementing a device or a system as previously described.

DETAILED DESCRIPTION OF THE INVENTION

Other features, details and advantages of the invention will emerge more clearly from the detailed description provided below for information.

Figure 1:
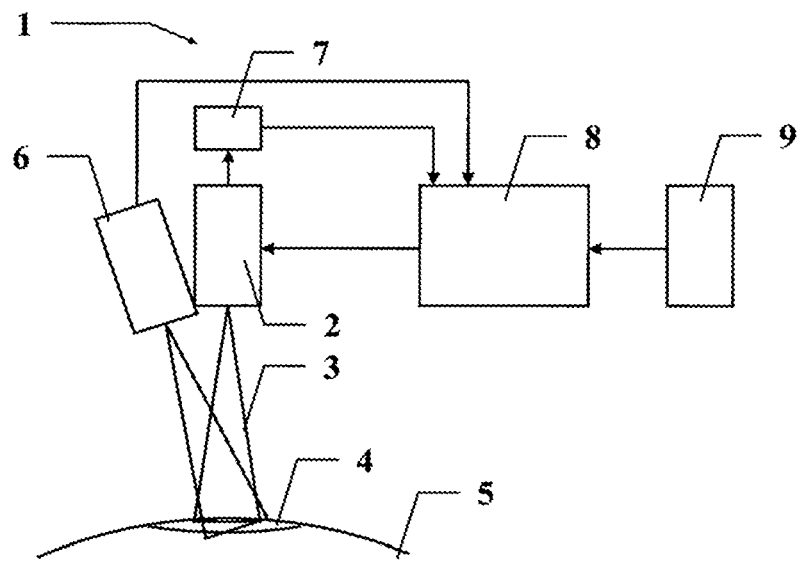
FIG. 1 schematically shows the device according to the invention.

As illustrated in FIG. 1, the dermatological treatment device 1 comprises a laser head 2, a pyrometer 6, a timer 7 and a control means 8. The laser head 2 is able to fire a laser beam 3 toward a target zone 4 located on the skin 5 of a patient. This illumination is intended to produce controlled heating of the skin 5 at the target zone 4. The pyrometer 6 is able to measure the temperature T of the skin 5 at said target 4, or in line with the surface of the skin receiving the shot of the laser beam 3. The timer 7 is able to determine the shot duration D of the laser head 2. The control means 8 is able to monitor the configuration and the operation of the laser head 2. It is thus responsible for activating or deactivating the laser shot and particularly managing in the associated safety.

The control means 8 can be electronic, computerized or a combination of the two. The configuration of the control means 8 is provided, by cabling, or more typically, by a program or software that the control means 8 is able to execute.

The device 1 may further comprise a man-machine interface 9. This man-machine interface can allow an operator to configure the device 1 by indicating the desired adjustments and makes it possible to command its use. During the use of the device 1, the beginning or activation of the laser shot is typically initiated by a command from the operator. Conversely, for securing purposes, the end or deactivation is commanded by the control means 8. Thus, the maximum quantity of energy transmitted to the target zone 4 remains continuously under the control of the control means 8.

Advantageously, the laser beam has a wavelength comprised between 0.8 μm and 2 μm, preferably between 0.9 and 1.8 μm, and particularly preferably between 1 and 1.6 μm.

Now, and in one preferred embodiment, the laser beam has a wavelength of about 1200 nm (e.g., 1210 nm).

According to one advantageous feature, the control means 8 is configured to deactivate the laser firing once at least one of two conditions is met. A first condition is related to the temperature T of the target zone 4 as measured by the pyrometer 6. The first condition for stopping the laser firing is met when the temperature T reaches a threshold temperature St.

A second condition is related to the duration D of the laser shot as measured by the timer 7. The second condition for stopping the laser firing is met when the duration of the laser firing reaches a duration threshold Sd.

The laser shot is stopped once at least one of these two conditions, and therefore the fastest, is met.

The temperature threshold St is advantageously a constant.

According to one specific embodiment, the temperature threshold St applied by the control means 8 weighted by the temperature offset (St−b) is less than or equal to the objective temperature To and the average heating coefficient C is less than 3, preferably less than 2.2.

Advantageously, the temperature threshold St is then comprised between 50 and 56° C., the average heating coefficient C is comprised between 1.10 and 2.10, preferably comprised between 1.30 and 1.90, the offset b being comprised between 2.5 and 4.5, preferably equal to 3.5, and the objective temperature is comprised between 53.5 and 59° C., preferably equal to 56° C.

Advantageously, the temperature threshold St is equal to 50° C., the average heating coefficient C is equal to 1.6, the offset b is equal to 3.5 and the objective temperature is equal to 56° C.

Here, the temperature T is regularly measured by the pyrometer 6 and updated during the progression of a laser shot. This updated temperature value T is, upon each update, compared with the temperature threshold value St in order to test whether the first condition is met.

The duration threshold Sd is advantageously a decreasing function of the temperature T. Thus, the higher the temperature T is initially, the shorter the duration Sd of the laser shot is.

Regarding the implementation of the two safeties (connected with St and Sd, respectively) causing deactivation of the laser, there are two possible scenarios.

In the scenario where the safety relates to the threshold temperature St that causes deactivation of the laser, the temperature T is measured once at the beginning of the laser shot and is used, via said function, to determine a maximum duration Sd of the shot. The temperature of the skin is regularly measured from the beginning moment of the laser shot. Once the skin reaches the threshold temperature (St) and even if the duration of the shot has not reached the threshold Sd, the firing of the laser is stopped (first safety).

In the second scenario, where the safety relates to the maximum duration of the shot that causes the deactivation of the laser, the temperature T is also measured once at the beginning of the laser shot and is used, here again via said function, to determine a maximum duration Sd of the shot. The temperature of the skin is measured regularly from the beginning moment of the laser shot. Once the maximum firing duration Sd is reached, and even if the temperature of the skin has not reached the threshold temperature, the firing of the laser is stopped here again (second safety). Now, and regarding the duration of the firing, it is possible to consider reevaluating it one or more times during firing. With this reevaluation, it is possible to perform monitoring as close as possible to any variation that may occur in the performance of the laser firing and/or the behavior of the skin response.

The function that determines the duration threshold is advantageously an affine function with form $Sd=(To-T-b)/C$, with Sd the duration threshold, T the temperature, To an objective temperature, b being a temperature offset and C an average heating coefficient of the skin.

Advantageously, the average heating coefficient C and the objective temperature To are constants.

Thus calculated, considering that the heating of the skin 5 can be modeled by a linear gain model equal to the average heating coefficient C, the duration threshold Sd constitutes an estimate of the time necessary for the skin 5 to go from the temperature T to the objective temperature To. If everything happens as anticipated, the second stopping condition is met when the skin 5 reaches the objective temperature (minus the temperature offset).

Figure 2:
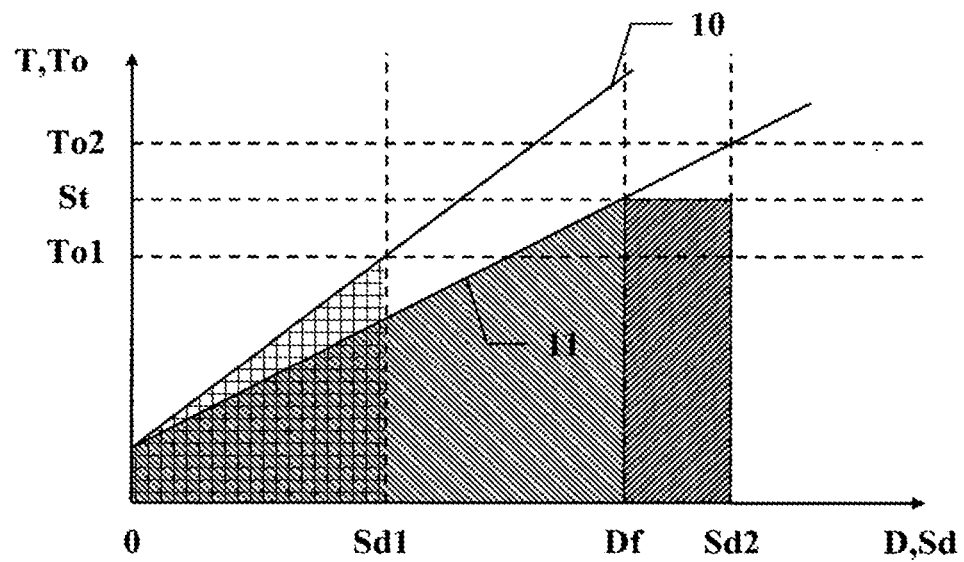
FIG. 2 shows a diagram of the duration as a function of the temperature.

FIG. 2 shows a temperature T/duration D diagram. Such a diagram can show an operating point of the skin 5 subject to a laser shot and its evolution over the duration. A temperature limit St determines the first condition for stopping a laser shot. An operating point may not be located above this horizontal limit St. A duration limit Sd determines the second condition for stopping a laser shot. An operating point may not be located in line with this vertical limit.

It appears that the two conditions for stopping the laser shot are closely related in that they contribute, together, to securing the device 1. Thus, all of the parameters for the first condition: St, and the second condition: C, To, must be considered and determined together, in order to cooperate effectively.

According to a first embodiment, the second condition, determining a duration threshold Sd with the form $Sd=(To-T-b)/C$, uses a higher coefficient C and an objective temperature To below the temperature threshold St. The temperature T of the skin then follows a faster heating C along the curve 10, with a steeper slope C. The objective temperature is To1, below the temperature threshold St. It follows that the duration threshold is determined equal to Sd1.

In such an embodiment, the objective temperature To1 is just reached at the duration Sd1, where the laser shot is stopped. Here, it is the second condition, for duration, that limits the laser shot. The first condition, for temperature, here is only present as a backup, for example in order to prevent overheating of the skin that could cause a burn. The operating points can be located in the cross-ruled zone.

A functional and usable example of such an embodiment uses the following parameters: a temperature threshold St equal to 53° C., an average heating coefficient C equal to 1.60, an offset b equal to 3.5 and an objective temperature To equal to 56° C. This example is functional and used experimentally. However, several encountered incidents have led to modifying it.

According to a second embodiment, the second condition, determining a duration threshold Sd with form Sd=(To−T−b)/C, uses a lower coefficient C but an objective temperature To above the temperature threshold St. The temperature T of the skin then follows a slower heating C along the curve 11, with a gentler slope C. The objective temperature is To2, greater than the temperature threshold St. It follows that the duration threshold is determined equal to Sd2.

In such an embodiment, the objective temperature To2 is in principle not reached. The temperature climb is supposed to be slower and accompanied by a longer duration threshold, here Sd2. A shot potentially lasts longer. Here, the first condition, for temperature, that limits the laser shot, and ends it at the final duration Df, corresponding to reaching the temperature St. The second condition, for duration, is, however, also present and makes it possible, if applicable, to extend the firing duration up to the duration Sd2, in order to increase the chances of reaching the temperature St. The operating points can be located in the crosshatched zone according to a first hatching mode going up to Df, which can thus extend, at most, up to Sd2 and include the crosshatched zone according to a second hatching mode.

This second embodiment thus advantageously significantly increases the likelihood of reaching the temperature threshold St, which is then advantageously set at an optimal treatment value. This makes it possible to obtain better efficacy in that the variability of the thermal behavior of the skin is thus taken into account from one patient to another. The second embodiment offers an increased duration to try to reach an effective temperature St. Thus, if one patient has a heating coefficient lower than the average heating coefficient C, his slower thermal response is offset by an increased firing duration. This increases the likelihood of correctly treating such a patient.

One functional and usable example of such an embodiment uses the following parameters: a temperature threshold St equal to 50° C., an average heating coefficient C equal to 1.6, an offset b equal to 3.5 and an objective temperature To equal to 56° C. The heating coefficient C is an average coefficient obtained by a measurement campaign done on a patient population. The preceding average heating coefficient C of 1.98 was determined using a population primarily made up of healthy patients. The new average heating coefficient C of 1.6 is more realistic in that it is determined using a population primarily made up of patients likely to be treated by the device 1.

The use of the temperature threshold St no longer as a safety but as a nominally decisive condition for stopping the laser firing leads to revising its value downwardly. On the contrary, the objective temperature has been increased, in order to increase the duration threshold Sd and thus the likelihood of reaching the temperature threshold St.

The two conditions for stopping laser firing of the device 1 are advantageously not configurable by the operator, in order to avoid any risk of burn and/or inefficacy of the treatment.

However, one possibility for configuring the objective temperature To is advantageously implanted in the control means 8, to allow an adjustment of the builder or maintenance type, accessible only to an authorized person who knows the risks. However, the configuration latitude for the objective temperature To is strictly limited, according to a variation of +/−0.7° C. around the nominal value of To.

Preferably, still another safety can be implanted in the dermatological treatment device. This safety observes the variation speed of the temperature T of the skin, as measured by the pyrometer 6, and commands an immediate stop of the laser shot if this elevation of the temperature T of the skin is either too fast or too slow relative to its theoretical value.

This makes it possible to detect an atypical behavior of the skin and thus to avoid either a lack of efficacy of the treatment in case of excessively slow temperature increase, or on the contrary a burn risk in case of excessively fast temperature increase.

The variation speed of the temperature T of the skin is determined by observing the variation of the measured temperature T of the skin as a function of time/duration D. This variation is regularly measured during a use of the device 1 and compared to its theoretical value. This theoretical value, using a linear model D=$\Delta$T/C, or $\Delta$T=C·D, like before, is the slope of the variation curve of the temperature T as a function of the duration D is equal to the average heating coefficient C.

Consequently, once the variation of the temperature as a function of time is either too low or too high, relative to the value of the selected average heating coefficient C, the laser shot is stopped immediately.

For information, it is considered that a value is too high or too low if it differs from its theoretical value by more than 10%.

The invention also relates to a dermatological treatment system by laser beam, said system comprising a device as previously described and interaction means between said device and the target zone to be treated, said interaction means being arranged to cooperate with said control means.

More particularly, said interaction means may comprise an adhesive substrate provided with identification means (e.g., RFID chip) capable of being fixed near the target zone to be treated, and communicating with an interface (e.g., by radio frequency) linked to said control means.

Such interaction means are known from international applications PCT WO 2007/080239 and PCT WO 2008/107563 and will therefore not be described here in more detail.

The invention makes it possible to carry out a terminological treatment method comprising the following steps:
  directing the laser beam of a device as previously described on a surface of the target zone of skin to be treated of a patient,
  measuring, using the pyrometer previously described, the temperature of the surface of skin contained in its field of view, said skin surface being completely comprised in the skin zone treated by said device, and slaving said light source to said measuring means such that the temperature of the treated skin zone is comprised between 45 and 60° C.

The invention claimed is:

1. A dermatological treatment device comprising a laser head able to fire a laser shot towards a target region of the skin of a patient, a pyrometer capable of measuring the temperature (T) of the skin in said target region and monitoring a variation of the temperature of the skin dynamically over time, a timer capable of measuring the duration (D) of the laser shot, and a control means capable of selectively activating or deactivating a laser shot, characterized in that the control means is configured to deactivate the laser shot when the duration (D) of the shot reaches a duration threshold in seconds (Sd) as determined by a linear function in the form Sd=(to−T−b)/C, where T is the measured temperature (T) of the skin, To is an objective temperature, b is a temperature offset, and C is an average heating coefficient of the skin, said duration threshold (Sd) being determined immediately before or immediately after a beginning of the laser shot and being reevaluated during the laser shot.

2. The device according to claim 1, where the control means is also configured to deactivate the laser shot when the temperature (T) reaches a temperature threshold (St).

3. The device according to claim 2, where the temperature threshold (St) weighted by the temperature offset (St b) is less than or equal to the objective temperature (To) and the average heating coefficient (C) is less than 3° C.·s$^{-1}$.

4. The device according to claim 3, where the temperature threshold (St) is comprised between 50 and 56° C., the temperature offset b is comprised between 2.5° C. and 4.5° C., the average heating coefficient (C) is comprised between 1.1° C.·s$^{-1}$ and 2.1° C.·s$^{-1}$, and the objective temperature (To) is comprised between 53.5 and 59° C.

5. The device according to claim 4, where the average heating coefficient (C) is comprised between 1.3° C.·s$^{-1}$ and 1.9° C.·s$^{-1}$.

6. The device according to claim 5, where the temperature threshold (St) is equal to 50° C., the average heating coefficient (C) is equal to 1.6° C.·s$^{-1}$, the offset b is equal to 3.5° C.·s$^{-1}$ and the objective temperature (To) is equal to 56° C.

7. The device according to claim 2, where the temperature threshold (St) weighted by the temperature offset (St b) is less than or equal to the objective temperature (To) and the average heating coefficient (C) is less than 2.2° C.·s$^{-1}$.

8. The device according to claim 1, where the objective temperature (To) is configurable according to a variation of +/−0.7° C. around its nominal value.

9. The device according to claim 1, is also configured to deactivate the laser shot when the variation of the measured temperature (T) of the skin based on the duration (D) differs by more that 10 percent from its theoretical value equal to the average heating coefficient (C).

10. A dermatological treatment system by laser beam, said system comprising:
   i) a device as defined in claim 1, and ii) interaction means between said laser head and the target region of the skin to be treated, said interaction means being arranged to cooperate with said control means.

11. A dermatological treatment device comprising a laser head able to fire a laser shot towards a target region of the skin of a patient, a pyrometer capable of measuring the temperature (T) of the skin in said target region and monitoring the variation of the temperature of the skin with dynamically over time, a timer capable of measuring the duration (D) of the laser shot, and a control means capable of selectively activating or deactivating a laser shot, characterized in that the control means is configured to deactivate the laser shot when the duration (D) of the shot reaches a duration threshold in seconds (Sd) as determined by a linear function in the form Sd−(To−T−b)/C, where T is the measured temperature (T) of the skin, To is an objective temperature, b is a temperature offset, and C is an average heating coefficient of the skin, said duration threshold (Sd) being determined in the second following the beginning of the laser shot and being reevaluated during the laser shot.

* * * * *